(12) United States Patent
Aimoto

(10) Patent No.: US 6,277,958 B1
(45) Date of Patent: Aug. 21, 2001

(54) METHOD FOR PREPARING PEPTIDE THIOL ESTER

(75) Inventor: Saburho Aimoto, 3-8-3, Motogamanaka-cho, Higashinada-ku, Kobe-shi, Hyogo-ken 658-0016 (JP)

(73) Assignees: Saburho Aimoto, Hyogo-ken; Susuma Kuwajima, Chiba-ken, both of (JP)

( * ) Notice: Subject to any disclaimer, the term of this patent is extended or adjusted under 35 U.S.C. 154(b) by 0 days.

(21) Appl. No.: 09/200,757

(22) Filed: Nov. 27, 1998

(51) Int. Cl.$^7$ .............................. C07K 17/00; C07K 1/00; G01N 33/00
(52) U.S. Cl. ..................... 530/334; 530/333; 530/335; 530/336; 530/337; 530/339; 530/345; 436/86; 436/89; 436/90
(58) Field of Search ..................... 530/334, 333, 530/335, 336, 337, 339, 345; 436/86, 89, 90

(56) References Cited

U.S. PATENT DOCUMENTS 5,827,825 * 10/1998 Takei et al. ............................ 514/12

OTHER PUBLICATIONS

Horiki; *Chemical Abstracts*, vol. 87, p. 651 Ref.#184937e, 1997 (Synth. Commun. 1997, 7(4),251–9).*

Uehi et al., *Chemistry Letters*, vol. 4, pp. 721–724, 1993.*

* cited by examiner

*Primary Examiner*—Christopher S. F. Low
*Assistant Examiner*—Abdel A. Mohamed
(74) *Attorney, Agent, or Firm*—Marina V. Schneller; Venable

(57) ABSTRACT

The present invention provides a method for producing a peptide thiol ester using fluoren-9-ylmethoxycarbonylamino acid (Fmoc-amino acid). The method is for peptide synthesis and involves (1) using and removing the Fmoc group bound as the protective group to the amino group of amino acid, fixed on a resin via the thiol ester bond, a specific reagent is used to remove an Fmoc group from the amino acid thiol ester resin; (2) adding Fmoc-amino acid to the Fmoc-freed resin and then removing the Fmoc group, repeatedly, to prepare the Fmoc-peptide thiol ester resin; and (3) treating sequentially, the Fmoc-peptide thiol ester resin with a cleavage reagent and with a reagent capable of removing the Fmoc group.

14 Claims, No Drawings

SEQUENCE LISTING

<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Asp(OBut)
<220> FEATURE:
<221> NAME/KEY: MOD_RES
<222> LOCATION: (2)

```
<223> OTHER INFORMATION: Thr(But)
<220> FEATURE:
<221> NAME/KEY: MOD_RES
<222> LOCATION: (4)
<223> OTHER INFORMATION: Thr(But)
<220> FEATURE:
<221> NAME/KEY: MOD_RES
<222> LOCATION: (6)
<223> OTHER INFORMATION: Lys(Boc)
<220> FEATURE:
<221> NAME/KEY: MOD_RES
<222> LOCATION: (8)
<223> OTHER INFORMATION: Gly(S-CH2CH2-CO)
<220> FEATURE:
<223> OTHER INFORMATION: this peptide has an amidated C-terminus

<400> SEQUENCE: 1

Asp Thr Phe Thr Val Lys Val Gly
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Gly(S-CH2CH2-CO)
<220> FEATURE:
<223> OTHER INFORMATION: this peptide has an amidated C-terminus

<400> SEQUENCE: 2

Asp Thr Phe Thr Val Lys Val Gly
 1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Asp(OBut)
<220> FEATURE:
<221> NAME/KEY: MOD_RES
<222> LOCATION: (2)
<223> OTHER INFORMATION: Asp(OBut)
<220> FEATURE:
<221> NAME/KEY: MOD_RES
<222> LOCATION: (3)
<223> OTHER INFORMATION: Asp(OBut)
<220> FEATURE:
<221> NAME/KEY: MOD_RES
<222> LOCATION: (4)
<223> OTHER INFORMATION: Thr(But)
<220> FEATURE:
<221> NAME/KEY: MOD_RES
<222> LOCATION: (6)
<223> OTHER INFORMATION: Thr(But)
<220> FEATURE:
<221> NAME/KEY: MOD_RES
<222> LOCATION: (8)
<223> OTHER INFORMATION: Lys(Boc)
<220> FEATURE:
<221> NAME/KEY: MOD_RES
<222> LOCATION: (10)
<223> OTHER INFORMATION: Gly(S-C(CH3)2CH2-CO)
<220> FEATURE:
<223> OTHER INFORMATION: this peptide has an amidated C-terminus
```

```
<400> SEQUENCE: 3

Asp Asp Asp Thr Phe Thr Val Lys Phe Gly
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Gly(S-C(CH3)2CH2-CO)
<220> FEATURE:
<223> OTHER INFORMATION: this peptide has an amidated C-terminus

<400> SEQUENCE: 4

Asp Asp Asp Thr Phe Thr Val Lys Phe Gly
 1               5                  10

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Cys(Acm)
<220> FEATURE:
<221> NAME/KEY: MOD_RES
<222> LOCATION: (25)
<223> OTHER INFORMATION: Gly(S-C(CH3)2CH2-CO)
<220> FEATURE:
<223> OTHER INFORMATION: this peptide has an amidated C-terminus

<400> SEQUENCE: 5

Thr Pro Asp Cys Val Thr Gly Lys Val Glu Tyr Thr Lys Tyr Asn Asp
 1               5                  10                  15

Asp Asp Thr Phe Thr Val Lys Val Gly
            20                  25

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: Gly(S-CH2CH2-CO)
<220> FEATURE:
<221> NAME/KEY: MOD_RES
<222> LOCATION: (6)
<223> OTHER INFORMATION: beta-alanine

<400> SEQUENCE: 6

Pro Phe Gly Phe Gly Xaa
 1               5

<210> SEQ ID NO 7
<211> LENGTH: 5
<212> TYPE: PRT
```

-continued

```
<213> ORGANISM: Artificial Sequence
<220> FEATURE:
<223> OTHER INFORMATION: cyclo peptide
<220> FEATURE:
<223> OTHER INFORMATION: Description of Artificial Sequence: Synthetic
      peptide

<400> SEQUENCE: 7

Pro Phe Gly Phe Gly
 1               5
```

METHOD FOR PREPARING PEPTIDE THIOL ESTER

FIELD OF INVENTION

This invention relates to a method for producing a peptide thiol ester, and, more particularly, the method which uses a fluoren-9-ylmethoxycarbonyl amino acid (Fmoc-amino acid).

BACKGROUND OF THE INVENTION

Peptides have been synthesized by condensation of amino acids. The peptide synthesis methods fall into two general categories; liquid-phase and solid-phase. The liquid-phase method has disadvantages, resulting from use of a solution, of being highly time consuming and labor intensive before it is completed, because the intermediate must be extracted from the solution, refined and confirmed whenever amino acid is added to, and chain length elongation is conducted in the solution. The solid-phase method elongates the peptide chain by a simple procedure in which an activated amino acid derivative is condensed consecutively on a resin on which amino acid with the protected amino terminals is and removing the protective group for the amino terminals. It is a simple peptide-synthesis method, much more efficient than the liquid-phase method.

One of the solid-phase methods uses t-butoxycarbonyl amino acid (hereinafter "Boc-amino acid"). It immobilizes Boc-amino acid on a resin, and condenses activated Boc-amino acid, while removing the Boc groups as the protective group for the amino terminals. It needs a large quantity of a halogen-containing compound, such as trifluoroacetic acid and methylene chloride, to remove the Boc group, and also needs a strong acid, such as anhydrous hydrogen fluoride to take peptide out of the resin in the final stage. A peptide thiol ester can be easily synthesized by the aid of Boc-amino acid. Nevertheless, however, this method involves environmental and safety-related problems, resulting from use of a halogen-containing compound and strong acid.

Another solid-phase method uses fluoren-9-ylmethoxycarbonyl amino acid (hereinafter "Fmoc-amino acid"). It condenses Fmoc-amino acid, while removing the Fmoc groups as the protective group for the amino groups with the aid of an amine compound, such as piperidine. It has been widely used, because of its advantages of dispensing with a halogen-containing compound for elongating the peptide chains and a strong acid for taking peptide out of the resin. This method, although preferable in terms of environment and safety, has an inherent disadvantage, when applied to synthesis of peptide thiol ester: peptide thiol ester shows high reactivity with the amine, decomposing the thiol ester bond to prevent and vitiate peptide chain elongation.

It is an object of the present invention to provide a method for producing a peptide thiol ester relatively easily, while reducing problems related to environmental preservation and safety. It is highly desirable to provide a synthetic scheme which does not require halogen containing compounds such as methylene chloride and which does not require reagents which reduce yields by reacting with desired intermediates. Such a method is very useful for synthesis of peptides, such as a long-chain peptides and cyclopeptides, and, at the same time, can be widely used for a variety of medicines from peptides as the starting stocks.

SUMMARY OF THE INVENTION

In accordance with the invention, the Fmoc group as a protective group is bound to the α-amino groups of amino acid(s), fixed on a resin via a thiol ester bond; the protective group can be removed by the aid of a specific reagent to remove the Fmoc group without causing decomposition of the thiol ester bond.

The present invention provides a method for producing a peptide thiol ester of formula (1):

$$H-A_1-B-S-X \qquad (1)$$

(In which each of $A_1$ and B is an amino acid residue; and X is a component bound to a sulfur atom to constitute the thiol ester)

The method comprises stages (1) to (4):

In Stage (1) a fluoren-9-ylmethoxycarbonyl amino acid derivative (Fmoc-amino acid derivative) is reacted with a resin, to produce an Fmoc-amino acid thiol ester resin, shown by the formula (2):

$$\text{Fmoc-B-S-X-Resin} \qquad (2)$$

(Fmoc is fluoren-9-ylmethoxycarbonyl; B and X are the same as the above; and Resin is a synthetic resin).

In Stage (2) the Fmoc-amino acid thiol ester resin, produced by Stage (1), is reacted with a reagent capable of removing the Fmoc group, to produce an amino acid thiol ester resin, shown by the formula (3):

$$H-B-S-X\text{-Resin} \qquad (3)$$

(B, X and Resin are the same as the above).

In Stage (3) the amino acid thiol ester resin, produced by Stage (2), is reacted with Fmoc-amino acid to produce an Fmoc-peptide thiol ester resin shown by the formula (4):

$$\text{Fmoc-}A_1\text{-B-S-X-Resin} \qquad (4)$$

(Fmoc, $A_1$, B, X and Resin are the same as the above).

In Stage (4) the Fmoc-peptide thiol ester resin, produced by Stage (3), is reacted with a cleavage reagent, to produce an Fmoc-peptide thiol ester, shown by the formula (5):

$$\text{Fmoc-}A_1\text{-B-S-X} \qquad (5)$$

(Fmoc, $A_1$, B and X are the same as the above); and it is either preceded by or followed by the reaction of the Fmoc-peptide thiol ester with a reagent capable of removing the Fmoc group. Thus the Fmoc-peptide thiol ester resin, produced by Stage (3), is reacted with a reagent capable of removing the Fmoc group before or after it is treated with a cleavage reagent, to produce a peptide thiol ester shown by the formula (1):

$$H-A_{1-B}-S-X \qquad (1)$$

($A_1$ and B are each an amino acid residue; and X is a component bound to a sulfur atom to constitute the thiol ester).

In another embodiment the present invention provides a method for producing a peptide thiol ester shown by the formula (6):

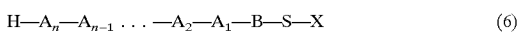
$$H-A_n-A_{n-1}\ldots-A_2-A_1-B-S-X \qquad (6)$$

($A_n, A_{n-1} \ldots A_2, A_1$ and B are each an amino acid residue; X is a component bound to a sulfur atom to constitute the thiol ester; and n is a positive integer) by the following stages (1) to (4):

In Stage (1) a fluoren-9-ylmethoxycarbonyl amino acid derivative (Fmoc-amino acid derivative) is reacted with a resin, to produce an Fmoc-amino acid thiol ester resin, shown by the formula (2):

Fmoc-B—S—X-Resin (2)

(Fmoc is fluoren-9-ylmethoxycarbonyl; B and X are the same as the above; and Resin is a synthetic resin).

In Stage (2) the Fmoc-amino acid thiol ester resin, produced by Stage (1), is reacted with a reagent capable of removing the Fmoc group, to produce an amino acid thiol ester resin, shown by the formula (3):

H—B—S—X-Resin (3)

(B, X and Resin are the same as the above).

In Stage (3) the amino acid thiol ester resin, produced by Stage (2), is reacted with Fmoc-amino acid to produce an Fmoc-peptide thiol ester resin shown by the formula (4):

Fmoc-$A_1$—B—S—X-Resin (4)

(Fmoc, $A_1$, B, X and Resin are the same as the above). The Fmoc-peptide thiol ester resin is then subjected to procedures similar to Stages (2) and (3) above, to remove the Fmoc group, and then to add Fmoc-amino acid to the resultant peptide thiol ester resin repeatedly (n—1) times, to produce a Fmoc-peptide thiol ester resin shown by the formula (7):

Fmoc-$A_n$—$A_{n-1}$ ... —$A_2$—$A_1$—B—S—X-Resin (7)

(Fmoc, $A_n$, $A_{n-1}$ ... $A_2$, $A_1$, B, X and Resin are the same as the above; and n is a positive integer).

In Stage (4) the Fmoc-peptide thiol ester resin, produced by Stage (3), is reacted with a cleavage reagent, to produce an Fmoc-peptide thiol ester, shown by the formula (8):

Fmoc-$A_n$—$A_{n-1}$ ... —$A_2$—$A_1$—B—S—X (8)

(Fmoc, $A_n$, $A_{n-1}$ ... $A_2$, $A_1$, B, X and n are the same as the above), preceded by or followed by the reaction of the Fmoc-amino thiol ester with a reagent capable of removing the Fmoc group. The Fmoc-amino thiol ester resin, produced by Stage (3), is reacted with a reagent capable of removing the Fmoc group before or after it is treated with a cleavage reagent, to produce a peptide thiol ester shown by the formula (6):

H—$A_n$—$A_{n-1}$ ... —$A_2$—$A_1$—B—S—X (6)

($A_n$, $A_{n-1}$ ... $A_2$, $A_1$ and B are each an amino acid residue; X is a component bound to a sulfur atom to constitute the thiol ester; and n is a positive integer).

DETAILED DESCRIPTION OF THE PRESENT INVENTION

The present invention is described in detail, below:

[Stage 1]

Stage (1) a fluoren-9-ylmethoxycarbonyl amino acid derivative (Fmoc-amino acid derivative) is contacted and reacted with a resin, to produce an Fmoc-amino acid thiol ester resin, shown by the formula (2):

Fmoc-B—S—X-Resin (2)

(Fmoc is fluoren-9-ylmethoxycarbonyl; B and X are the same as the above; and Resin is a synthetic resin).

The reaction of a fluoren-9-ylmethoxycarbonyl amino acid derivative (Fmoc-amino acid derivative) with a resin is not limited, so long as the Fmoc-amino acid derivative can be fixed on the resin via the thiol ester bond. Such a reaction may be represented by the following formula (9) or (10):

Fmoc-NH—$CHR_1$—CO—S—$CR_2R_3$—$CH_2$—CO—OH+$NH_2$-Resin→Fmoc-NH—$CHR_1$—CO—S—$CR_2R_3$—$CH_2$—CO—NH-Resin (9)

(Fmoc and Resin are the same as the above; and $R_1$, $R_2$ and $R_3$ are each hydrogen, an alkyl or aryl group, independently).

(10)

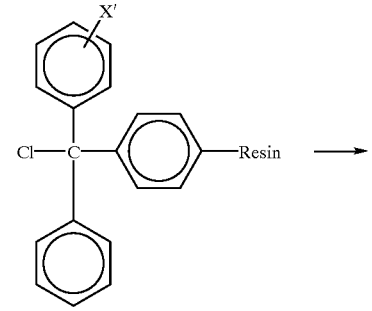
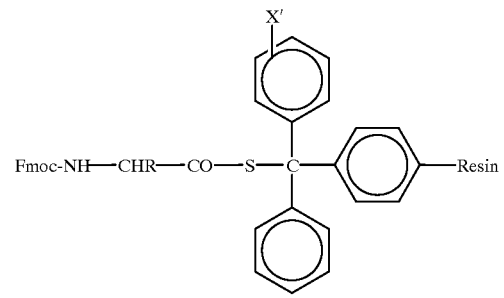

(Fmoc and Resin are the same as the above; and R is hydrogen, an alkyl or aryl group; and X' is a substituent).

Furthermore, the reaction shown by the formula (11) is also useful for the present invention:

Fmoc-NH—CHR—CO—OH+HS-Resin→Fmoc-NH—CBR—CO—S-Resin (11)

Fmoc, R and Resin are the same as the above).

The foregoing reaction of the Fmoc-amino acid derivative with the resin is not limited, and can be effected over a wide range of reaction conditions. In general, the reaction is conducted at 10 to 30°C. for 5 to 60 minutes in a solvent, such as 1-methyl-2-pyrrolidinone(1-methyl-2-pyrrolidone). In embodiments below, all the peptide syntheses were carried out under ambient conditions.

The amino acid that is used in the Fmoc-amino acid derivative is not limited, and known amino acid(s) can be freely used for the amino acid sequence of the objective peptide thiol ester. Table 1 shows some examples of naturally-occurring amino acid useful for the present invention. In this specification, an amino acid compound and its amino acid residue are represented by the sign corresponding to that of the amino acid. Amino acid having L-configuration is marked with a sign of L-.

TABLE 1

| Amino acid | Sign | Amino acid | Sign |
|---|---|---|---|
| Aliphatic amino acid | | | |
| Straight-chain amino acid | | Amide | |
| Glycine | Gly | Asparagine | Asn |
| Alanine | Ala | Glutamine | Gln |
| Branched amino acid | | Basic amino acid | |
| Valine | Val | Lysine | Lys |
| Leucine | Leu | Arginine | Arg |
| Isoleucine | Ile | S-containing amino acid | |
| Cycloamino acid | | Cystine | Cys |
| (Imino acid) | | Methionine | Met |
| Proline | Pro | | |
| Hydroxyamino acid | | | |
| Serine | Ser | | |
| Threonine | Thr | | |
| Acidic amino acid | | | |
| Aspartic acid | | | |
| Glutamic acid | | | |
| Aromatic amino acid | | Heterocyclic amino acid | |
| Phenylalanine | Phe | Tryptophan | Trp |
| Tyrosine | Tyr | Histidine | His |

The resin used in the method of the present invention is not limited, so long as it can fix the Fmoc-amino acid derivative thereon. In certain embodiments, the resin will contain thiol, amino or halogen (e.g. chlorine; fluorine) substituents. In general, the resin is a synthetic resin, such as polystyrene and polyacrylamide, preferably containing said thiol, amino or halogen substituents.

[Stage (2)]

In Stage (2) the Fmoc-amino acid thiol ester resin, produced by the step (1), is reacted with a reagent capable of removing the Fmoc group, to produce an amino acid thiol ester resin, shown by the formula (3):

$$\text{H—B—S—X-Resin} \tag{3}$$

(B, X and Resin are the same as the above).

It is essential to use a specific reagent capable of removing the Fmoc group, for the reaction to remove the Fmoc group from the Fmoc-amino acid thiol ester resin. Such a reagent is a basic compound represented by 1-methylpyrrolidine or hexamethyleneimine. These compounds may be used alone and/or neat or in combination, or dissolved in a solvent, such as 1-methyl-2-pyrrolidinone(1-methyl-pyrrolidone) or dimethyl sulfoxide, or mixed with another compound. The reagent can be also used after being mixed with a reagent represented by 1-hydroxybenzotriazole or 2,4-dinitrophenol. For example, in embodiments below, ten-times volume to the weight of a resin (mL/g) is sufficient enough to remove the Fmoc groups.

[Stage (3)]

In Stage (3) the amino acid thiol ester resin, produced by Stage (2), is reacted with Fmoc-amino acid to produce an Fmoc-peptide thiol ester resin shown by the formula (4):

$$\text{Fmoc-}A_1\text{—B—S—X-Resin} \tag{4}$$

($A_1$ and B are each an amino acid residue; and Fmoc, X and Resin are the same as the above).

In another embodiment of Stage (3), the Fmoc-peptide thiol ester resin, produced by the above reaction of Stage (3), is subjected to the procedures similar to Stages (2) and (3) above, to remove the Fmoc groups, and Fmoc-amino acid is added to the resultant peptide thiol ester resin repeatedly (n−1)times, to produce an Fmoc-peptide thiol ester resin shown by the formula (7):

$$\text{Fmoc-}A_n\text{—}A_{n-1}\ldots\text{—}A_2\text{—}A_1\text{—B—S—X-Resin} \tag{7}$$

($A_n, A_{n-1} \ldots A_2, A_1$ and B are each an amino acid residue, Fmoc, X and Resin are the same as the above; and n is a positive integer).

As described above, amino acid can be added in sequence to elongate the peptide chain, without decomposing the thiol ester bond in the Fmoc-peptide thiol ester resin, by repeatedly adding Fmoc-amino acid to the peptide thiol ester resin, after removing the Fmoc group from the Fmoc-peptide thiol ester resin. Amino acid added are selected from well-known amino acids to elongate the peptide chain, depending on the amino acid sequence in the objective peptide thiol ester.

[(4)]

In (4) the Fmoc-peptide thiol ester resin, produced by Stage (3), is reacted with a cleavage reagent, to take the Fmoc-peptide thiol ester, shown by the formula (5):

$$\text{Fmoc-}A_1\text{—B—S—X} \tag{5}$$

(Fmoc, $A_1$, B and X are the same as the above) from the Fmoc-peptide thiol ester resin, and then reacts the resultant Fmoc-peptide thiol ester with a reagent capable of removing the Fmoc group, to produce the peptide thiol ester, shown by the formula (1):

$$\text{H—}A_1\text{—B—S—X} \tag{1}$$

($A_1$, B and X are the same as the above).

In another embodiment of Stage (4) the Fmoc-peptide thiol ester resin, produced by Stage (3), is reacted with the above reagent capable of removing the Fmoc group and then with the cleavage reagent, to produce the peptide thiol ester, shown by the formula (1):

$$\text{H—}A_1\text{—B—S—X} \tag{1}$$

($A_1$, B and X are the same as the above).

In still another embodiment of Stage (4) the Fmoc-peptide thiol ester resin, produced by Stage(3) by repeatedly adding Fmoc-amino acid, and is reacted with a cleavage reagent, to remove the Fmoc-peptide thiol ester, shown by the formula (8):

$$\text{Fmoc-}A_n\text{—}A_{n-1}\ldots\text{—}A_2\text{—}A_1\text{—B—S—X} \tag{8}$$

(Fmoc, $A_n, A_{n-1} \ldots A_2, A_1$, B, X and n are the same as the above) from the Fmoc-peptide thiol ester resin, and then the resultant Fmoc-peptide thiol ester is reacted with the above reagent capable of removing the Fmoc group, to produce the peptide thiol ester, shown by the formula (6):

$$\text{H—}A_n\text{—}A_{n-1}\ldots\text{—}A_2\text{—}A_1\text{—B—S—X} \tag{6}$$

($A_n, A_{n-1} \ldots A_2, A_1$, B, X and n are the same as the above).

In still another embodiment of Stage (4) the Fmoc-peptide thiol ester resin, produced by Stage(3) by repeatedly adding Fmoc-amino acids is reacted with the above reagent capable of removing the Fmoc group and then with the cleavage reagent, to produce the peptide thiol ester, shown by the formula (6):

$$H\text{—}A_n\text{—}A_{n-1}\ldots\text{—}A_2\text{—}A_1\text{—}B\text{—}S\text{—}X \qquad (6)$$

($A_n$, $A_{n-1}$ ... $A_2$, $A_1$, B, X and n are the same as the above).

The cleavage reagent useful for the present invention is a weak acid, such as trifluoroacetic acid. Trifluoroacetic acid may be mixed with ethane dithiol, phenol, water, thioanisole or the like. A thiol compound may be used to take the Fmoc-peptide thiol ester from the Fmoc-peptide thiol ester resin. In embodiments below, twenty-times volume to the weight of a protected peptide resin (mL/g) is used for cleavage of peptide from a resin.

In accordance with the invention, the peptide thiol ester can be synthesized by above s Stages (1) to (4), while minimizing use of environmental pollutants and reducing danger in the synthetic process. Type and number of amino acid to be condensed on the thiol ester resin depend on the amino acid sequence in the objective peptide thiol ester. Number of condensation is normally in a range from 2 to 50. The reactions in Steps (1) to (4) can be easily effected by using a commercially available, automatic peptide synthesizer. Such a synthesizer is supplied by Advanced ChemTech (Multipeptide synthesizer, ACT series) and Applied Biosystem (Peptide synthesizer 433). The as-synthesized product is generally low in purity, because of the presence of defective peptides. It is refined in the final stage by an adequate method, e.g., high-pressure liquid chromatography (HPLC), to produce a high-purity Fmoc-peptide thiol ester or peptide thiol ester.

A long-chain peptide can be produced from the peptide thiol ester produced by the method of the present invention, using known chemical reactions. A cyclopeptide can be easily synthesized by reacting the peptide thiol ester resin or peptide thiol ester with an active ester-constituting component, either alone or in the presence of silver ions. Examples of such a component include thiophenol. The peptide thiol ester produced by the method of the present invention can be also used as the starting stock for production of a peptide in which amino acid is condensed to a high degree.

EXAMPLES

The present invention is described more fully by the following preferred embodiments, which by no means limit the present invention.

The Resin used in Examples 1–3 (Fmoc-NH-SAL Resin, is available from Watanabe Chemical Ind. Ltd); it comprises (a) monomer: 99% styrene and 1% divinylbenzee, and (b) functional group: 4-(α-[2',4'-dimethoxyphenyl]-aminomethyl)-phenoxy group The MBHA resin (MBHA resin HCI, Watanabe Chemical Ind. Ltd): used in Example 4 comprises (a) monomer: 99% styrene and 1% divinylbenzene and (b) functional group: 4-(α-[4'-methylphenyl]-aminomethyl)-phenyl group Example 1

Fmoc-Gly-S—$CH_2CH_2$—CO—OH, synthesized from Fmoc-glycine (supplied by Peptide Institute Inc.) and β-mercaptopropionic acid (supplied by Nacalai Tesque), was reacted with a resin (supplied by Watanabe Chemical Ind. Ltd.), to form the Fmoc-Gly-S—$CH_2CH_2$—CO—NH-Resin, which was used as the starting material. The glycine content was 0.36 mmol/g-resin.

100 mg of the Fmoc-Gly-S—$CH_2CH_2$—CO—NH-Resin thus prepared was washed with 1 ml of dimethylformamide for 1 min, and further washed 4 times in the same manner. It was then subjected to the following Procedure 1 through Procedure 4 repeatedly, to elongate the peptide chain. The Fmoc-amino acid types were those of L-Val, L-Lys(Boc), L-Val, L-Thr(Bu$^t$), L-Phe, L-Thr(Bu$^t$) and L-Asp(OBu$^t$), used consecutively, wherein Boc is t-butoxycarbonyl group, Bu$^t$ is t-butyl group and OBu$^t$ is t-butyl ester group, all of which were protective groups for the amino acid residue.

(Procedure 1)

The above Fmoc-Gly-S—$CH_2CH_2$—CO—NH-Resin was reacted with 1 ml of a reagent solution (A) to remove the Fmoc group (shown in Table 2), which was added to the above, at 25° C. for 2 min with stirring. The above procedure was repeated under the same conditions with 1 ml of the reagent solution (A), to prepare an H-Gly-S—$CH_2CH_2$—CO—NH-Resin.

TABLE 2

| Composition of the reagent (A) to remove the Fmoc group | |
|---|---|
| 1-methyl pyrrolidine | 25 ml |
| Hexamethyleneimine | 2 ml |
| 1-hydroxybenzotriazole | 2 g |
| Mixed solvent of NMP/DMSO* | balance |
| | (Total 100 ml) |

*Volume Ratio: 1/1; NMP: 1-methyl-2-pyrrolidinone (1-methyl-2-pyrrolidone); and (Procedure 2)

The H-Gly-S—$CH_2CH_2$—CO—NH-Resin, obtained by Procedure 1, was washed with 1 ml of dimethyl formamide (DMF) at 25° C. for 1 min. It was then further washed 5 times with 1 ml of 1-methyl-2-pyrrolidone (NMP) at 25° C. for 1 min.

(Procedure 3)

The H-Gly-S—$CH_2CH_2$—CO—NH-Resin, obtained by Procedure 2, was reacted with 0.75 ml of an NMP solution (A) containing 0.3 mmol of Fmoc-amino acid and 0.3 mmol of 1-hydroxybenzotriazole, and 0.25 ml of another NMP solution (B) containing 0.3 mmol of diisopropylcarbodiimide, which were added to the H-Gly-S—$CH_2CH_2$—CO—NH-Resin, at 25° C. for 50 min with stirring. The resin thus prepared was washed 3 times with 1 ml of NMP, and again reacted with 0.75 ml of the NMP solution (A) and 0.25 ml of the NMP solution (B) at 25° C. for 50 min, to prepare the Fmoc-peptide thiol ester resin with one amino acid molecule added.

(Procedure 4)

The Fmoc-peptide thiol ester resin, obtained by Procedure 3, was washed 5 times with 1 ml of NMP at 25° C. for 1 min. It was then washed 5 times with 1 ml of DMF at 25° C. for 1 min.

Procedure 1 through 4 were repeated, to prepare the Fmoc-peptide thiol ester resin with the peptide chain, shown by the formula (12):

Fmoc-L-Asp(OBu$^t$)-L-Thr(Bu$^t$)-L-Phe-L-Thr(Bu$^t$)-L-Val-L-Lys-(Boc)-L-Val-Gly-S—$CH_2CH_2$—CO—NH-Resin SEQ ID NO:1 (12)

The Fmoc-peptide thiol ester was prepared from the above Fmoc-peptide thiol ester resin in the following manner. The Fmoc-peptide thiol ester resin was treated with 4ml of a mixed solvent of 82.5% of trifluoroacetic acid, 2.5% of ethane dithiol, 5% of phenol, 5% of water and 5% of thioanisole at room temperature for 3 h, to remove the protective group for the side chain. At the same time, the Fmoc-peptide thiol ester was taken out of the resin, and precipitated using cooled diethyl ether added. The precipitate was dissolved in a mixed solvent of water and acetonitrile, and filtered. The filtrate was freeze-dried into the crude Fmoc-peptide thiol ester powder.

The crude Fmoc-peptide thiol ester was purified by the reverse-phase, high-pressure liquid chromatography (Nacalai Tesque, Cosmosil 5C18AR), to produce 4.0 mg of the Fmoc-peptide thiol ester, shown by the formula (13):

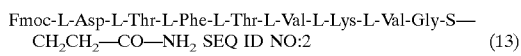

Fmoc-L-Asp-L-Thr-L-Phe-L-Thr-L-Val-L-Lys-L-Val-Gly-S—
    $CH_2CH_2$—CO—$NH_2$ SEQ ID NO:2                    (13)

The Fmoc-peptide thiol ester had the following properties: The mass spectrometric analysis results showed that $[M+H]^+$ was 1175.1 (m/z) (calculated value: 1175.4). The amino acid analysis results showed that Asp: 1.14, Thr: 1.78, Phe: 1.24, Val: 1.84, Lys: 0.99 and Gly: 1.00.

Example 2

Fmoc-Gly-S—$C(CH_3)CH_2$—CO—OH, synthesized from Fmoc-glycine (supplied by Peptide Institute Inc.) and HS—$C(CH_3)_2CH_2$—CO—OH (prepared by the inventor), was reacted with a resin (supplied by Watanabe Chemical Ind. Ltd.), to form the Fmoc-Gly-S—$C(CH_3)_2CH_2$—CO—NH-Resin, which was used as the starting material. The glycine content was 0.36 mmol/g-resin.

100 mg of the Fmoc-Gly-S—$C(CH_3)_2CH_2$—CO—NH-Resin thus prepared was washed with 1 ml of DMF for 1 min, and further washed 4 times in the same manner. It was then subjected to the following Procedure 1 through Procedure 4 repeatedly, to elongate the peptide chain. The Fmoc-amino acid types were those of L-Phe, L-Lys(Boc), L-Val, L-Thr (Bu$^t$), L-Phe, L-Thr(Bu$^t$), L-Asp(OBu$^t$), L-Asp(OBu$^t$) and L-Asp(OBu$^t$) used consecutively, wherein Boc is t-butoxycarbonyl group, Bu$^t$ is t-butyl group and OBu$^t$ is t-butyl ester group, all of which were protective groups for the amino acid residue.

(Procedure 1)

The above Fmoc-Gly-S—$C(CH_3)_2CH_2$—CO—NH-Resin was reacted with 1 ml of a reagent solution (B) to remove the Fmoc group (shown in Table 3), which was added to the above, at 25° C. for 2 min with stirring. The above procedure was repeated under the same conditions with 1 ml of the reagent solution (B), to prepare an H-Gly-S—$C(CH_3)_2CH_2$—CO—NH-Resin.

TABLE 3

Composition of the reagent (B) to remove the Fmoc group

| Hexamethyleneimine | 20 ml |
| 1-Hydroxybenzotriazole | 20 g |
| *NMP | balance |
| | (Total 100 ml) |

*NMP: 1-methyl-2-pyrrolidinone (1-methyl-2-pyrrolidone)

(Procedure 2)

The H-Gly-S—$C(CH_3)_2CH_2$—CO—NH-Resin, obtained by Procedure 1, was washed with 1 ml of DMF at 25° C. for 1 min. It was then further washed 5 times with 1 ml of NMP at 25° C. for 1 min.

(Procedure 3)

The H-Gly-S—$C(CH_3)_2CH_2$—CO—NH-Resin, obtained by Procedure 2, was reacted with 0.75 ml of an NMP solution (A) containing 0.3 mmol of Fmoc-amino acid and 0.3 mmol of 1-hydroxybenzotriazole, and 0.25 ml of another NMP solution (B) containing 0.3 mmol of diisopropylcarbodiimide, which were added to the H-Gly-S—$C(CH_3)_2CH_2$—CO—NH-Resin, at 25° C. for 50 min with stirring. The resin thus prepared was washed 3 times with 1 ml of NMP, and again reacted with 0.75 ml of the NMP solution (A) and 0.25 ml of the NMP solution (B) at 25° C. for 50 min, to prepare the Fmoc-peptide thiol ester resin with one amino acid molecule added.

(Procedure 4)

The Fmoc-peptide thiol ester resin, obtained by Procedure 3, was washed 5 times with 1 ml of NMP at 25° C. for 1 min. It was then washed 5 times with 1 ml of DMF at 25° C. for 1 min.

Procedure 1 through 4 were repeated, to prepare the Fmoc-peptide thiol ester resin with the peptide chain elongation, shown by the formula (14):

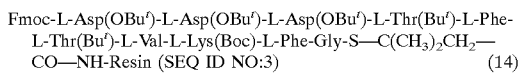

Fmoc-L-Asp(OBu$^t$)-L-Asp(OBu$^t$)-L-Asp(OBu$^t$)-L-Thr(Bu$^t$)-L-Phe-
    L-Thr(Bu$^t$)-L-Val-L-Lys(Boc)-L-Phe-Gly-S—$C(CH_3)_2CH_2$—
    CO—NH-Resin (SEQ ID NO:3)                          (14)

The Fmoc-peptide thiol ester was prepared from the above Fmoc-peptide thiol ester resin in the following manner. The Fmoc-peptide thiol ester resin was treated with 2 ml of a mixed solvent of 82.5% of trifluoroacetic acid, 2.5% of ethane dithiol, 5% of phenol, 5% of water and 5% of thioanisole at room temperature for 3 h, to remove the protective group for the side chain. At the same time, the Fmoc-peptide thiol ester was taken out of the resin, and precipitated using cooled diethyl ether added. The precipitate was dissolved in a mixed solvent of water and acetonitrile, and filtered. The filtrate was freeze-dried into the crude Fmoc-peptide thiol ester powder.

The crude Fmoc-peptide thiol ester was purified by the reverse-phase, high-pressure liquid chromatography (Nacalai Tesque, Cosmosil 5C18AR), to produce 6.0 mg of the Fmoc-peptide thiol ester, shown by the formula (15):

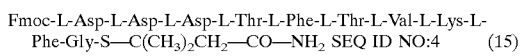

Fmoc-L-Asp-L-Asp-L-Asp-L-Thr-L-Phe-L-Thr-L-Val-L-Lys-L-
    Phe-Gly-S—$C(CH_3)_2CH_2$—CO—$NH_2$ SEQ ID NO:4    (15)

The Fmoc-peptide thiol ester had the following properties: The mass spectrometric analysis results showed that $[M+H]^+$ was 1482.1(m/z) (calculated value: 1481.6). The amino acid analysis results showed that Asp: 2.67, Thr: 1.53, Phe: 1.81, Val: 0.76, Lys: 0.85 and Gly: 1.00.

Example 3

Fmoc-Gly-S—$C(CH_3)_2CH_2$—CO—OH, synthesized from Fmoc-glycine (supplied by Peptide Institute Inc.) and HS—$C(CH_3)_2CH_2$—CO—OH (prepared by the inventor), was reacted with a resin (supplied by Watanabe Chemical Ind. Ltd.) to form 200 mg the Fmoc-Gly-S—$C(CH_3)_2CH_2$—CO—NH-Resin, which was used as the starting material. The glycine content was 0.20 mmol/g-resin.

200 mg of the Fmoc-Gly-S—$C(CH_3)_2CH_2$—CO—NH-Resin thus prepared was washed with 4 ml of NMP at room temperature for 1 min, and further washed 3 times in the same manner. It was then subjected to the following Procedure 1 through Procedure 4 repeatedly, to elongate the peptide chain. This elongation was effected using a peptide synthesizer (Applied Biosystems, Model 433). The Fmoc-amino acid types were those of Val, Lys, Val, Thr(Bu$^t$), Phe, Thr(Bu$^t$), Asp(OBu$^t$), Asp(OBu$^t$), Asp(OBu$^t$), Asn(Trt), Tyr (Bu$^t$), Lys, Thr(Bu$^t$), Tyr(Bu$^t$), Glu(OBu$^t$), Val, Lys, Gly, Thr(Bu$^t$), Val, Cys(Acm), Asp(OBu$^t$), Pro, and Thr(Bu$^t$) used consecutively, wherein Bu$^t$ is t-butyl group, OB$^t$ is t-butyl ester group, Trt is trityl group and Acm is acetamidomethyl group, all of which were protective groups for the amino acid residue.

(Procedure 1)

The above Fmoc-Gly-S—$C(CH_3)_2CH_2$—CO—NH-Resin was reacted with 4 ml of a reagent solution (A) to remove the Fmoc group (shown in Table 2), which was added to the above, at 25° C. for 2.9 min with stirring. The above procedure was repeated at 25° C. for 18 min with 4 ml of the reagent solution (A), to prepare an H-Gly-S—C(CH₃)₂CH₂—CO—NH-Resin.
(Procedure 2)

The H-Gly-S—C(CH₃)₂CH₂—CO—NH-Resin, obtained by Procedure 1, was washed with 4 ml of NMP at room temperature for 1 min. It was then further washed 6 times with 4 ml of NMP at 25° C. for 1 min.
(Procedure 3)

The H-Gly-S—C(CH₃)₂CH₂—CO—NH-Resin, obtained by Procedure 2, was reacted with the following solution, which were added to the above, at 25° C. for 10 min with stirring. The solution was prepared by the following procedure: (1) 1 mmol of Fmoc-amino acid was dissolved in 2 ml of a DMF solution containing 0.9 mmol of 1-hydroxybenzotriazole (HOBt) and 0.9 mmol of 2-(1H-benzotriazole-1-yl)-1,1,3,3-tetramethyluronium hexafluorophosphate (HBTU), (2) 1 ml of an NMP solution containing 2 mmol of diisopropylethylamine (DIEA) was added to the above solution, to activate the Fmoc-amino acid. The above solution prepared was added to, and reacted with, the H-Gly-S—C(CH₃)₂CH₂—CO—NH-Resin (obtained by Procedure 2). The resin thus prepared was washed 6 times with 4 ml of NMP for 1 min. Then, 5 ml of an NMP solution containing 0.5 mol of acetic anhydride, 0.125 mol of DIEA and 0.015 mol of HOBt was added to the above resin and stirred for 5.5 min, to acetylate the unreacted amino acid, thereby to prepare the Fmoc-peptide thiol ester resin with one amino acid residue added.
(Procedure 4)

The Fmoc-peptide thiol ester resin, obtained by Procedure 3, was washed 5 times with 4 ml of NMP at 25° C. for 1 min.

Procedure 1 through 4 were repeated, to prepare the Fmoc-peptide thiol ester resin with the elongated peptide chain, and the Fmoc-peptide thiol ester resin was subjected to the procedure similar to Procedure 1, to remove the Fmoc group, and thereby to prepare 350 mg of the peptide thiol ester resin, shown by the formula (16):

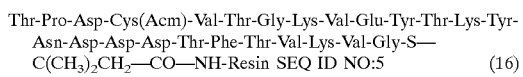

Thr-Pro-Asp-Cys(Acm)-Val-Thr-Gly-Lys-Val-Glu-Tyr-Thr-Lys-Tyr-Asn-Asp-Asp-Asp-Thr-Phe-Thr-Val-Lys-Val-Gly-S—C(CH₃)₂CH₂—CO—NH-Resin SEQ ID NO:5       (16)

The peptide thiol ester was prepared from the above peptide thiol ester resin in the following manner. The peptide thiol ester resin was treated with a mixed solvent of 82.5% of trifluoroacetic acid, 2.5% of ethane dithiol, 5% of phenol, 5% of water and 5% of thioanisole at room temperature for 3 h, to remove the protective group for the side chain. At the same time, the peptide thiol ester was taken out of the resin, and precipitated using cooled diethyl ether added. The precipitate was dissolved in a mixed solvent of water and acetonitrile, and filtered. The filtrate was freeze-dried into the crude peptide thiol ester powder.

The crude peptide thiol ester was purified by the reverse-phase, high-pressure liquid chromatography (Nacalai Tesque, Cosmosil 5C18AR), to produce the peptide thiol ester, shown by the formula (17), at a yield of 22% based on the glycine content of the resin as the starting material:

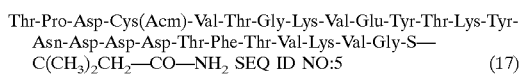

Thr-Pro-Asp-Cys(Acm)-Val-Thr-Gly-Lys-Val-Glu-Tyr-Thr-Lys-Tyr-Asn-Asp-Asp-Asp-Thr-Phe-Thr-Val-Lys-Val-Gly-S—C(CH₃)₂CH₂—CO—NH₂ SEQ ID NO:5       (17)

The Fmoc-peptide thiol ester thus produced had the following properties: The mass spectrometric analysis results showed that [M+H]⁺ was 2982.25 (m/z) (calculated value: 2982.35). The amino acid analysis results showed that Asp: 4.92, Thr: 4.57, Glu: 1.16, Gly: 2.06, Val: 4.12, Tyr: 2.22, Phe: (1), Lys: 2.91, Pro: 0.78, and 1/2Cys: undetected.

Example 4

4.95 g of a hydrochloride of 4-methylbenzhydrylamine resin (MBHA resin) containing 0.5 mmol/g-resin of amino group (supplied by Peptide Institute Inc.) was neutralized/washed, with shaking, in 40 ml of an NMP solution containing 5% of DIEA for 1 min. This procedure was further repeated 2 times, to produce the MBHA resin. The resin was washed with 40 ml of NMP, and this procedure was further repeated 2 times. 4.5 mmol of t-butoxycarbonyl β-alanine benzotriazole ester (Boc-β-Ala-Obt, prepared by the inventor), dissolved in 14 ml of NMP, was added to, and reacted with, the resin with stirring for 2.5 h. The reaction solution thus prepared was incorporated with 2.5 mmol of DIEA for further reaction for 20 h. The resin thus prepared was washed with 40 ml of NMP with stirring for 1 min. This procedure was further repeated 4 times. The resin was then treated with 40 ml of NMP containing 20% of acetic anhydride and 10% of DIEA for 10 min, to acetylate the unreacted amino group and thereby to produce the Boc-β-Ala-MBHA-Resin.

The resin thus prepared was washed 5 times with 40 ml of NMP for 1 min, further washed 3 times with 40 ml of methylene chloride for 1 min, and treated with 60 ml of a methylene chloride solution containing 50% of trifluoroacetic acid for 5 min. It was further treated, after the methylene chloride solution was removed, with 60 ml of the fresh methylene chloride solution for 20 min. The trifluoroacetate of H-β-Ala-MBHA-Resin thus prepared was washed 3 times with 40 ml of NMP for 1 min, further washed once with 40 ml of NMP for 0.5 min, and neutralized 3 times with an NMP solution containing 5% of DIEA.

The H-β-Ala-MBHA-Resin thus prepared was washed 3 times with 40 ml of NMP for 1 min, and then mixed and treated with 15 ml of NMP, dissolving 5.0 mmol of S-tritylmercaptopropionic acid benzotriazole ester (Trt-S—CH₂CH₂—CO-OBt, prepared by the inventor), at room temperature for 16 h. The Trt-S—CH₂CH₂—CO-β-Ala-MBHA-Resin thus prepared was washed 5 times with 40 ml of NMP for 1 min, and then treated with 20 ml of an NMP solution containing 20% of acetic anhydride and 10% of DIEA, to acetylate the unreacted mercapto group. It was then washed 5 times with 40 ml of NMP for 1 min, to produce 5.68 g of the Trt-S—CH₂CH₂—CO-β-Ala-MBHA-Resin. Its β-Ala content was 0.40 mmol/g-resin.

1.00 g of the Trt-S—CH₂CH₂—CO-β-Ala-MBHA-Resin thus prepared was treated with 10 ml of a trifluoroacetic acid solution containing 5% of 1,2-ethane dithiol for 5 min, and then the solution was removed. It was further treated 3 times in the same manner, but for 10, 20 and 30 min consecutively. The HS—CH₂CH₂—CO-β-Ala-MBHA-Resin thus prepared was washed 3 times with 10 ml of methylene chloride for 1 min, washed once with 10 ml of NMP for 0.5 min, and washed 3 times with 10 ml of an NMP solution containing 5% of DIEA. It was further washed with 10 ml of NMP for 1 min, and then reacted with 2.0 mmol of Fmoc-glycine benzotriazole ester (Fmoc-Gly-OBt), dissolved in 8 ml of NMP, at room temperature for 14 h. The resin was then washed 5 times with 10 ml of NMP for 1 min, to produce 1.12 g of the Fmoc-Gly-S—CH₂CH₂—CO-β-Ala-MBHA-Resin. Its glycine content was 0.30 mmol/g.

The Fmoc-Gly-S—CH₂CH₂—CO-β-Ala-MBHA-Resin thus prepared was washed with 40 ml of NMP at room temperature for 1 min, and then washed 3 times in the similar manner. It was then subjected to the following Procedure 1 through Procedure 4 repeatedly, to elongate the peptide chain. This elongation was effected using a peptide synthesizer (Applied Biosystems, Model 433). The Fmoc-amino acids used were those of Phe, Gly, Phe and Pro, used consecutively.

(Procedure 1)

The above Fmoc-Gly-S—CH$_2$CH$_2$—CO-β-Ala-MBHA-Resin was reacted with 4 ml of a reagent solution (A) to remove the Fmoc group (shown in Table 2), which was added to the above, at 25° C. for 2.9 min with stirring. The above procedure was repeated at 25° C. for 18 min with 4 ml of the reagent solution (A), to remove the Fmoc group and thereby to prepare an H-Gly-S—CH$_2$CH$_2$—CO-β-Ala-MBHA-Resin.

(Procedure 2)

The H-Gly-S—CH$_2$CH$_2$—CO-β-Ala-MBHA-Resin, obtained by Procedure 1, was washed with 4 ml of NMP at room temperature for 1 min. It was then further washed 6 times with 4 ml of NMP at 25° C. for 1 min.

(Procedure 3)

The H-Gly-S—CH$_2$CH$_2$—CO-β-Ala-MBHA-Resin, obtained by Procedure 2, was reacted with the following solution, which were added to the above, at 25° C. for 10 min with stirring. The solution was prepared by the following procedure: (1) 1 mmol of Fmoc-amino acid was dissolved in 2 ml of a DMF solution containing 0.9 mmol of HOBt and 0.9 mmol of HBTU, (2) 1 ml of an NMP solution containing 2 mmol of DIEA was added to the above solution, to activate the Fmoc-amino acid. The above solution prepared was added to, and reacted with, the H-Gly-S—CH$_2$CH$_2$—CO-β-Ala-MBHA-Resin (obtained by Procedure 2). The resin thus prepared was washed 6 times with 4 ml of NMP for 1 min. Then, 5 ml of an NMP solution containing 0.5 mol of acetic anhydride, 0.125 mol of DIEA and 0.015 mol of HOBt was added to the above resin and stirred for 5.5 min, to acetylate the unreacted amino acid, thereby to prepare the Fmoc-peptide thiol ester resin with one amino acid molecule added.

(Procedure 4)

The Fmoc-peptide thiol ester resin, obtained by Procedure 3, was washed 5 times with 4 ml of NMP at 25° C. for 1 min.

Procedure 1 through 4 were repeated, to prepare the Fmoc-peptide thiol ester resin with the elongated peptide chain, and the Fmoc-peptide thiol ester resin was subjected to the procedure similar to Procedure 1, to remove the Fmoc group, and thereby to prepare the peptide thiol ester resin, shown by the formula (18):

Pro-Phe-Gly-Phe-Gly-S—CH$_2$CH$_2$—CO-β-Ala-MBHA-Resin SEQ ID NO:6 (18)

A cyclopeptide was prepared from the above peptide thiol ester resin by the following procedure: 5.0 mg of the peptide thiol ester resin was suspended in 0.1 ml of an NMP solution containing 5% of thiophenol at room temperature or under heating, and stirred for 12 to 48 h. The crude cyclopeptide thus produced was purified by the reverse-phase, high-pressure liquid chromatography (Nacalai Tesque, Cosmosil 5C18AR), to produce the cyclopeptide, shown by the formula (19), at a yield of 8.6% based on the glycine content of the resin as the starting material:

Cyclo-(Pro-Phe-Gly-Phe-Gly)SEQ ID NO:7 (19)

The cyclopeptide thus produced had the following properties: The mass spectrometric analysis results showed that [M+H]$^+$ was 506.4 (m/z) (calculated value: 506.2). The amino acid analysis results showed that Gly: 2, Pro: 1.04, and Phe: 2.04.

As described above in detail and concretely, the method of the present invention for producing a peptide thiol ester (1) removes the Fmoc group bound as the protective group to the amino group of amino acid, fixed on a resin via the thiol ester moiety, by the aid of a specific reagent to remove a Fmoc group from the amino acid thiol ester resin, (2) adds Fmoc-amino acid to the Fmoc-freed resin and then removes the Fmoc group, repeatedly to prepare the Fmoc- peptide thiol ester resin, and (3) treats the Fmoc-peptide thiol ester resin with an a cleavage reagent and then with a reagent capable of removing the Fmoc group, or with a reagent capable of removing the Fmoc group and then with a cleavage reagent, in order to prepare the peptide thiol ester of desired amino acid sequence and number of peptide bonds, accurately and in high purity. Reduced environmental pollution and safety production are other advantages of the method of the present invention. The peptide thiol ester or Fmoc-peptide thiol ester as the intermediate, prepared by the method of the present invention, can be used as the starting materials to produce long-chain peptides or cyclopeptides very easily. Therefore, the method of the present invention contributes to development of various medicines from these peptides as the starting materials.

What is claimed is:

1. A method for producing a peptide thiol ester by a synthesis which does not require methylene chloride wherein the peptide thiol ester is characterized by formula (1)

H—A$_1$—B—S—X    (1)

wherein H is a hydrogen atom, S is a sulfur atom, each of A$_1$ and B is an amino acid residue; and X is a component bound to a sulfur atom to constitute the thiol ester, wherein the method comprises stage (1), stage (2), stage (3), and stage (4):

wherein Stage (1) comprises reacting a fluoren-9-ylmethoxycarbonyl amino acid derivative (Fmoc-amino acid derivative) with a resin, to produce an Fmoc-amino acid thiol ester resin, of formula (2):

Fmoc-B—S—X-Resin    (2)

wherein Fmoc is fluoren-9-ylmethoxycarbonyl; each of B, S and X is the same as the above; and Resin is a synthetic resin;

wherein Stage (2) comprises reacting the Fmoc-amino acid thiol ester resin, produced by Stage (1), with a reagent which removes the Fmoc group, to produce an amino acid thiol ester resin, of formula (3):

H—B—S—X-Resin    (3)

wherein each of H, B, S and X is the same as the above;

wherein Stage (3) comprises reacting the amino acid thiol ester resin, produced by Stage (2), with Fmoc-amino acid to produce the Fmoc-peptide thiol ester resin of formula (4):

Fmoc-A$_1$—B—S—X-Resin    (4)

wherein each of Fmoc, A$_1$, B, S, X, and Resin is defined as above; and wherein Stage (4) comprises either of the following two reactions:
(i) the Fmoc-peptide thiol ester resin is reacted with a cleavage reagent which removes the resin group, and then with a reagent which removes the Fmoc group to produce the peptide thiol ester of formula (1); or
(ii) the Fmoc-peptide thiol ester resin is reacted with a reagent which removes the Fmoc group, and then with a cleavage reagent which removes the resin group to produce the peptide thiol ester of formula (1).

2. The method of claim 1, wherein said reagent which removes the Fmoc group comprises at least one compound selected from the group consisting of 1-methylpyrrolidine and hexamethyleneimine.

3. The method of claim 1, wherein said reagent which removes the Fmoc group is a mixture of at least one compound selected from a group consisting of 1-methylpyrrolidine and hexamethyleneimine, and 1-hydroxybenzotriazole.

4. The method of claim 1, which comprises contacting the Fmoc-peptide thiol ester resin, produced by Stage (3), with at least one compound selected from the group consisting of 1-methylpyrrolidine and hexamethyleneimine.

5. The method of claim 1, which comprises contacting the Fmoc-peptide thiol ester resin, produced by Stage (3), with at least one compound selected from the group consisting of 1-methylpyrrolidine and hexamethyleneimine, and 1-hydroxybenzotriazole.

6. The method of claim 1, wherein the Fmoc-peptide thiol ester resin is reacted with a cleavage reagent which removes the resin group, and then with a reagent which removes the Fmoc group to produce the peptide thiol ester.

7. The method of claim 1, wherein the Fmoc-peptide thiol ester resin is reacted with a reagent which removes the Fmoc group, and then with a cleavage reagent which removes the resin group to produce the peptide thiol ester.

8. A method for producing a peptide thiol ester by a synthesis which does not require methylene chloride wherein the peptide thiol ester is characterized by a formula (6):

H—A$_n$—A$_{n-1}$ ... —A$_2$—A$_1$—B—S—X    (6)

wherein H is a hydrogen atom, S is a sulfur atom, each of A$_n$, A$_{n-1}$ ..., A$_2$, A$_1$ and B is an amino acid residue; X is a component bound to a sulfur atom to constitute a thiol ester; and n is a positive integer;

wherein the method comprises stage (1), stage (2), stage (3), and stage (4):

wherein Stage (1) comprises reacting a fluoren-9-ylmethoxycarbonyl amino acid derivative (Fmoc-amino acid derivative) with a resin, to produce an Fmoc-amino acid thiol ester resin, shown by the formula (2):

Fmoc-B—S—X-Resin    (2)

wherein Fmoc is fluoren-9-ylmethoxycarbonyl; B, S and X are the same as the above; and Resin is a synthetic resin;

wherein Stage (2) comprises reacting the Fmoc-amino acid thiol ester resin, produced by Stage (1), with a reagent which removes the Fmoc group, to produce an amino acid thiol ester resin, shown by the formula (3):

H—B—S—X-Resin    (3)

wherein each of H, B, S and X is the same as the above;

wherein Stage (3) comprises reacting the amino acid thiol ester resin, produced by Stage (2), with Fmoc-amino acid to produce an Fmoc-peptide thiol ester resin shown by the formula (4):

Fmoc-A$_1$—B—S—X-Resin  (4)

wherein each of Fmoc, A$_1$, B, S, X, and Resin is the same as above; and repeating Stages (2) and (3) above, repeatedly (n−1) times, to produce a Fmoc-peptide thiol ester resin of formula (7):

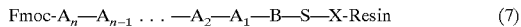

Fmoc-A$_n$—A$_{n-1}$ . . . —A$_2$—A$_1$—B—S—X-Resin  (7)

wherein each of Fmoc, A$_n$, A$_{n-1}$ . . . , A$_2$, A$_1$, B, S, X, and n is the same as the above; and wherein Stage (4) comprises either of the following two reactions:
(i) the Fmoc-peptide thiol ester resin is reacted with a cleavage reagent which remove the resin group, and then with a reagent which removes the Fmoc group to produce the peptide thiol ester of formula (6); or
(ii) the Fmoc-peptide thiol ester resin is reacted with a reagent which removes the Fmoc group, and then with a cleavage reagent which removes the resin group to produce the peptide thiol ester of formula (6).

9. The method of claim 8, wherein said reagent which removes the Fmoc group comprises at least one compound selected from a group consisting of 1-methylpyrrolidine and hexamethyleneimine.

10. The method of claim 8, wherein said reagent which removes the Fmoc group is a mixture of at least one compound selected from a group consisting of 1-methylpyrrolidine and hexamethyleneimine, and 1-hydroxybenzotriazole.

11. The method of claim 8, which comprises contacting the Fmoc-peptide thiol ester resin, produced by Stage (3), with at least one compound selected from the group consisting of 1-methylpyrrolidine and hexamethyleneimine.

12. The method of claim 8, which comprises contacting the Fmoc-peptide thiol ester resin, produced by Stage (3), with at least one compound selected from the group consisting of 1-methylpyrrolidine and hexamethyleneimine, and 1-hydroxybenzotriazole.

13. The method of claim 8, wherein the Fmoc-peptide thiol ester resin is reacted with a cleavage reagent which removes the resin group, and then with a reagent which removes the Fmoc group to produce the peptide thiol ester.

14. The method of claim 8, wherein the Fmoc-peptide thiol ester resin is reacted with a reagent which removes the Fmoc group, and then with a cleavage reagent which removes the resin group to produce the peptide thiol ester.

* * * * *